US006323391B1

(12) United States Patent
Schlaepfer et al.

(10) Patent No.: US 6,323,391 B1
(45) Date of Patent: Nov. 27, 2001

(54) METHODS AND TRANSGENIC MOUSE MODEL FOR IDENTIFYING AND MODULATING FACTORS LEADING TO MOTOR NEURON DEGENERATION

(75) Inventors: William W. Schlaepfer; Rafaela Cañete-Soler, both of Philadelphia, PA (US)

(73) Assignee: Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 09/489,979

(22) Filed: Jan. 21, 2000

Related U.S. Application Data

(60) Provisional application No. 60/117,007, filed on Jan. 25, 1999.

(51) Int. Cl.[7] .......................... A01K 67/027; G01N 33/00
(52) U.S. Cl. .................................................. 800/18; 800/3
(58) Field of Search ............................................ 800/3, 18

(56) References Cited

PUBLICATIONS

Wall, 1996. Theriogenology, 45:57–68.*
Houdebine, 1994. Journal of Biotechnology, 34:269–287.*
Kappell, et al., 1992. Current Opinion in Biotechnology, 3:548–553.*
Hodgson, 1995. Exp. Opin. Ther. Patents, 5(5):459–468.*
Mullins, et al., 1996. Journal of Clinical Investigation, 98(11):S37–S40.*
Canet–Soler, Nov., 1997, Molecular Biology of the Cell, Abstracts, vol. 8, p. 323a.*
Bruijn, L.I. and Cleveland, D.W., "Mechanisms of selective motor neuron death in ALS: insights from transgenic mouse models of motor neuron disease", *Neuropathol. Appl. Neurobiol.*, 1996, 22:373–387.
Cañete–Soler et al., "Mutation in Neurofilament Transgene Implicates RNA Processing in the Pathogenesis of Neurodegenerative Disease", *J. Neurosci.*, 1999, 19 (4):1–11.
Cañete–Soler et al., "Stability Determinants Are Localized to the 3'–Untranslated Region and 3'–Coding Region of the Neurofilament Light Subunit mRNA Using a Tetracycline–inducible Promoter", *J. Biol. Chem.*, 1998, 273:12650–12654.

Cañete–Soler et al., "Characterization of Ribonucleoprotein Complexes and Their Binding Sites on the Neurofilament Light Subunit mRNA", *J. Biol. Chem.*, 1998, 273:12655–12661.
Cañete–Soler et al., "Mutation in Neurofilament Transgene Implicates RNA Processing in the Pathogenesis of Neurodegenerative Disease", *J. Neurosci.*, 1999, 19:1273–1283.
Cañete–Soler and Schlaepfer, Division of Neuropathology, University of Pennsylvania, Similar poly (c)–sensitive RNA–binding complexes regulate the stability of the heavy and light neurofilament mRNAs 1–30.
Carden et al., "Two–Stage Expression of Neurofilament Polypeptides During Rat Neurogenesis with Early Establishment of Adult Phosphorylation Patterns", *J. Neurosci.*, 1987, 7:3489–3504.
Chomczynski, P. and Sacchi, N., "Single–Step Method of RNA Isolation by Acid Guanidinium Thiocyanate–Phenol–Chloroform Extraction", *Anal. Biochem.*, 1987, 162:156–159.
Collard et al., "Defective axonal transport in a transgenic mouse model of amyotrophic lateral sclerosis", *Nature*, 1995, 375:61–64.
Cote et al., "Progressive Neuronopathy in Transgenic Mice Expressing the Human Neurofilament Heavy Gene: A Mouse Model of Amyotrophic Lateral Sclerosis", *Cell*, 1993, 73:35–46.
Couillard–Despres et al., "Protective effect of neurofilament heavy gene overexpression in motor neuron disease induced by mutant superoxide dismutase", *Proc. Nat'l Acad. Sci. USA*, 1998, 95:9629–9630.
Elder et al., "Absence of the Mid–sized Neurofilament Subunit Decreases Axonal Calibers, Levels of Light Neurofilament (FL–L), and Neurofilament Content", *J. Cell Biol.*, 1998, 141:727–739.
Eyer et al., "Pathogenesis of two axonopathies does not require axonal neurofilaments", *Nature*, 1998, 391:584–587.

(List continued on next page.)

*Primary Examiner*—Deborah Crouch
*Assistant Examiner*—Anne-Marie Baker
(74) *Attorney, Agent, or Firm*—Licata & Tyrrell P.C.

(57) ABSTRACT

Methods are provided for identifying factors involved in motor neuron degeneration by identifying factors affected by alterations in a C-binding complex of a ribonucleotide protein complex, isolating and purifying the factors or nucleic acid sequences; and examining the neuropathic effect of the factors or nucleic acid sequences encoding the factors in a transgenic mouse. Also provided is a transgenic mouse model which expresses a mutant transgenic NF mRNA and exhibits degeneration of motor neurons. This model can be used to test, screen and identify factors and nucleic acid sequences encoding factors causing degeneration of motor neurons.

2 Claims, No Drawings

OTHER PUBLICATIONS

Eyer, J. and Peterson, A.C., "Neurofilament–Deficient Axons and Perikaryal Aggregates in Viable Transgenic Mice Expressing a Neurofilament–β–Galactosidase Fusion Protein", *Neuron,*1994, 12:389–405.

Fisher, C.L. and Pei, G.K., "Modification of a PCR–based Site–Directed Mutagenesis Method", *BioTechniques,* 1997, 23:570–574.

Gill et al., "Assembly Properties of Dominant and Recessive Mutations in the Small Mouse Neurofilament (NF–L) Subunit", *J. Cell Biol.,* 1990, 111:2005–2019.

Karaosmanoglu et al., "Regional Differences in the Number of Neurons in the Myenteric Plexus of the Guinea Pig Small Intestine and Colon: An Evaluation of Markers Used to Count Neurons", *Anat. Rec.,* 1996, 244:470–480.

Lee et al., "Monoclonal Antibodies Distinguish Several Differentially Phosphorylated States of the Two Largest Rat Neurofilament Subunits (NF–H and NF–M) and Demonstrate Their Existence in the Normal Nervouse System of Adult Rats", *J. Neurosci.,* 1987, 7:3473–3488.

Lee et al., "A Mutant Neurofilament Subunit Causes Massive, Selective Motor Neuron Death: Implications for the Pathogenesis of Human Motor Neuron Dissease", *Neuron,* 1994, 13:975–988.

Schwartz et al., "Axonal Dependency of the Postnatal Upregulation in Neurofilament Expression", *J. Neurosci. Res.,* 1990, 27:193–201.

Schlaepfer, W.W. and Bruce, J., Simultaneous U–Regulation of Neurofilament Proteins During the Postnatal development of the Rat Nervous System, *J. Neurosci. Res.,* 1990, 25:39–49.

Schwartz et al., "Actinomycin Prevents the Destabilization of Neurofilament mRNA in Primary Sensory neurons", *J. Biol. Chem.* 1992, 267:24596–24600.

Schwartz et al., "Stabilization of neurofilament transcripts during postnatal development", *Mol. Brain Res.,* 1994, 27:215–220.

Williamson et al, "Absence of neurofilaments reduces the selective vulnerability of motor neurons and slows disease caused by a familial amyotrophic lateral Sclerosis–linked superoxide dismutase 1 mutant", *Proc. Nat'l Acad. Sci USA,* 1998, 95:9631–9636.

Wong et al., "Increasing Neurofilament Subunit NF–M Expression Reduces Axonal NF–H, Inhibits Radial Growth, and Results in Neurofilamentous Accumulation in Motor Neurons", *J. Cell Biol.,* 1995, 130:1413–1422.

Yamasaki et al., "Defective Expression of Neurofilament Protein Subunits in Hereditary Hypotrophic Axonopathy of Quail", *Lab. Invest.,* 1992, 66:734–743.

Xu et al., "Increased Expression of Neurofilament Subunit NF–L Produces Morphological Alterations That Resemble the Pathology of Human Motor Neuron Disease", *Cell,* 1993, 73:23–33.

Zhu et al., "Delayed Mutation of Regenerating Myelinated Axons in Mice Lacking Neurofilaments", *Exp. Neurol.,* 1997, 148:299–316.

* cited by examiner

SEQUENCE LISTING

<160> NUMBER OF SEQ ID NOS: 2

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic

<400> SEQUENCE: 1
ctcatttctg aagaggactt gatttgagcc ctattcccaa ctattcc                47

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic

<400> SEQUENCE: 2
ttcagaaatg agcttttgct ccatatcttt cttcttagcc acc                    43

METHODS AND TRANSGENIC MOUSE MODEL FOR IDENTIFYING AND MODULATING FACTORS LEADING TO MOTOR NEURON DEGENERATION

This application claims the benefit of priority from Provisional Application Ser. No. 60/117,007, filed Jan. 25, 1999.

INTRODUCTION

This invention was supported in part by funds from the U.S. Government (National Institutes of Health Grant Nos. NS15722 and NS37552) and the U.S. Government may therefore have certain rights in the invention.

BACKGROUND OF THE INVENTION

Stabilization of neurofilament (NF) mRNAs is a critical phenomena in determining levels of NF expression, axonal size and rate of axonal conduction. By regulating NF mRNA stability, the neuron is able to establish fundamental functional parameters of its own phenotype. The stabilization of NF mRNA and increased levels of NF expression are strongly influenced by the nature of target cell innervation and, presumably, by feedback signals from the target cells to the parent neuron. The feedback signals regulating NF expression arise during a developmental timeframe in which feedback signals from the target cells are also promoting the survival and further development of the parent neuron. The latter phenomena are believed to involve growth factors produced by the target cell which interact with receptors on the parent neuron and prevent the parent neuron from undergoing apoptosis. Neurons that reach and innervate target cells acquire growth factors and survive, while neurons that fail to innervate target cells do not acquire growth factors and undergo apoptosis. Growth factors thereby enable the developing neurons to override an intrinsic program of apoptosis, as exemplified by the inability of the developing neuron to survive when separated from the target cell by nerve transection or when grown in vitro in the absence of growth factors. During the next phase of development (between 0 and 4 weeks of postnatal development), neurons lose their dependence on growth factors for survival, as exemplified by their ability to survive in vitro in the absence of growth factors as well as by their ability to survive a nerve transection (Schwartz et al., *J. Neurosci. Res.*, 1990, 27:193–201). The weaning of neurons of their dependence on growth factors for survival reflects a change in the expression of genes regulating apoptosis, possibly due to the recruitment of a new set of genes which serve to override apoptosis in the absence of growth factors. While the identity of these anti-apoptosis genes are unknown, it is significant that they impart a vital and unique property to the neuron during the same developmental timeframe in which there is dramatic upregulation in the expression of the three NF genes (Schlaepfer, W. W. and Bruce, J., *J. Neurosci. Res.*, 1990, 25:39–49). The dramatic increase of NF expression is due to the stabilization of NF mRNAs (Schwartz et al., *J. Biol. Chem.* 1992, 267:24596–24600 and Schwartz et al., *Mol. Brain Res.*, 1994, 27:215–220) and is mediated by factors that bind to the NF mRNAs (Cañete-Soler et al., *J. Biol. Chem.*, 1998, 273:12650–12654; and Cañete-Soler et al., *J. Biol. Chem.*, 1998, 273:12655–12661). If these same factors regulate the expression of anti-apoptotic genes that maintain neuronal homeostasis in the absence of growth factors, the factors themselves would be an important vehicle by which to identify the anti-apoptotic gene products that maintain neuronal homeostasis.

The possibility that the same regulatory factors alter post-transcriptional expression of NF genes and gene products maintaining neuronal homeostasis derives from studies of motor neuron degeneration in transgenic mice bearing neurofilament transgenes. Although the pathogenesis of motor neuron degeneration due to expression of a mutant NF-L transgene (Lee et al., *Neuron*, 1994, 13:975–988) or overexpression of a wild-type NF-L (Xu et al., *Cell*, 1993, 73:23–33) or NF-H (Cote et al., *Cell*, 1993, 35–45) transgene in transgenic mice is presently unknown, it has been generally assumed that the neuropathic effects result from expression of NF protein by the transgene. It has been further assumed that the additional expression of NF protein by the transgene causes motor neuron degeneration by disrupting NF assembly or transport in NF-rich motor neurons (Collard et al., *Nature*, 1995,375:61–64; Bruijn, L. I. and Cleveland, D. W., *Neuropathol. Appl. Neurobiol.*, 1996, 22:373–387).

The interpretation that the pathogenesis of experimental motor neuron degeneration is due to alterations in protein function, however, is problematic on several grounds. While NF accumulations are prima facie evidence of disrupted NF transport, they do not indicate whether disrupted transport is a cause, rather than a result, of neuronal degeneration. Accumulation of NFs is a frequent and readily detectable pathological change that does not necessarily lead to a progressive loss of neuronal viability, even with massive accumulations of NFs in motor neurons (Eyer, J. and Peterson, A. C., *Neuron*, 1994, 12:389–405). Nor is there appreciable loss of neuronal viability from a marked depletion of NFs due to ablation of NF-L (Zhu et al., *Exp. Neurol.*, 1997, 148:299–316) or medium neurofilament subunit (NF-M) (Elder et al., *J. Cell Biol.*, 1998, 141:727–739) or a spontaneous nonsense mutation of NF-L (Yamashaki et al., *Lab. Invest.*, 1992, 66:734–743). Finally, there is the issue of specificity, as to why a widely and abundantly expressed neuronal protein should lead to the selective degeneration of a very small subset of neurons. It is also unclear why experimental motor neuron degeneration occurs from overexpression of a mouse NF-L (Xu et al., *Cell*, 1993, 73:23–33) or a human heavy neurofilament subunit (NF-H; Cote et al., *Cell*, 1993, 73:35–46) transgene, but not from overexpression of an NF-M (Wong et al., *J. Cell Biol.*, 1995, 130:1413–1422) or a chimeric NF-H/lacZ (Eyer, J. and Peterson, A. C., *Neuron*, 1994, 12:389–405) transgene.

More recently, the effects of NF expression on other models of motor neuron degeneration have been examined by cross breeding transgenic lines of mice. These studies have shown that neither the time-course nor neuropathological effects of primary sensory neuronal degeneration in (wst/wst) wasted mice or primary motor neuron degeneration in SOD-1G37R mutant mice are altered by the presence of a mutant NF-H transgene (NF-H/lacZ) causing massive maldistribution of NFs within the afflicted neurons (Eyer et al., *Nature*, 1998, 391:584–587). On the other hand, the additional expression from a wild-type, full-length human NF-H transgene was found to prolong the lifespan and reduce the neuropathologic effects on motor neurons of the same SOD-1G37R transgenic mice (Couillard-Despres et al., *Proc. Nat'l Acad. Sci. USA*, 1998, 95:9629–9630). Motor neuron degeneration by an SOD-1 transgene was also slowed by ablation of the endogenous NF-L gene, thereby markedly reducing NF expression (Williamson et al., *Proc. Nat'l Acad. Sci USA*, 1998, 95:9631–9636). Paradoxically, the ablation of the NF-L gene enhanced the pathological effects of the mutant SOD-1 transgene on primary sensory neurons.

The severe neuropathic effects that result from low level expression of a mutant NF-L transgene (Lee et al. *Neuron*, 1994, 13:975–988) contrast with the mild neuropathic effects that result from overexpression of the wild-type NF-L (Xu et al., *Cell*, 1993, 73:23–33) transgene, thus indicating that a mutation in the NF-L transgene markedly enhances the neuropathic effects of the transgene in transgenic mice. This mutant NF-L transgene, however, contained two separate mutations, namely, a leucine-to-proline point mutation in the rod domain of the protein and a 36 bp c-myc tag that was appended to the carboxyl terminus of the protein. The c-myc tag was added in order to mark the NF-L protein from the transgene and distinguish it from the wild-type NF-L protein encoded by the endogenous NF-L gene of the mouse. The leucine-to-proline point mutation in the rod domain was intended to create a dominant disassembling subunit that leads to the disassembly of all NFs in the cell (Gill et al. *J. Cell Biol.*, 1990, 111:2005–2019). Although the neuropathic effects of the transgene were attributed to the point mutation in the rod domain, this interpretation was not supported by a close examination of degenerating motor neurons. Close examination showed that expression of the mutant NF-L subunit did not lead to a granular disintegration of NFs, as characteristic of the dominant disassembly phenotype (Gill et al. *J. Cell Biol.*, 1990, 111:2005–2019), nor prevent the accumulation of assembled NFs, admixed with mutant protein, in cell bodies and dystrophic neurites of the degenerating motor neurons. The inability of the mutant protein to disrupt NFs in degenerating motor neurons indicates that the mutation does not have a dominant disassembly phenotype in vivo and that the accumulation of NFs are, most likely, the result rather than the cause of the degenerative state of motor neurons. Furthermore, the inability of the point mutation to alter assembled NFs also negates the role of this mutation in mediating neuropathic effects. Hence, there must be an alternative explanation accounting for the enhanced neuropathic effect of the mutant NF-L transgene on motor neurons of transgenic mice.

It is now believed that the enhanced neuropathic effects of the mutant NF-L transgene on motor neurons of transgenic mice (Lee et al. *Neuron*, 1994, 13:975–988) are not due to the point mutation in the rod domain of the protein, but rather to the second mutation created by insertion of the c-myc tag onto the carboxyl terminus of the protein. While the addition of the c-myc tag does not alter the ability of a NF protein subunit to assemble into filaments (Gill et al. *J. Cell Biol.*, 1990, 111:2005–2019), the placement of the 36 bp c-myc tag at the junction between the coding region and 3'UTR of the NF-L cDNA generates a mutant NF-L mRNA that may have altered biological properties. The discovery that the c-myc mutation in the NF-L transcript was inadvertently inserted into the major stability determinant of the transcript supports this view (Cañete-Soler et al., *J. Biol. Chem.*, 1998, 12650–12654 and Cañete-Soler et al., *J. Biol. Chem.*, 1998, 12655–12661). Thus, the neuropathic effects are believed to be due to the c-myc mutation in the NF-L mRNA. Further, expression of the mutant NF-L mRNA, not the mutant NF-L protein, is believed to mediate the neuropathic effects of the mutant transgene in transgenic mice. This discovery has profound implications regarding the pathogenesis of motor neuron degeneration in transgenic mice and on potential treatments and cures of motor neuron diseases.

The biological effects of a c-myc mutation in the NF-L transcript and the ability of NF-L mRNA, not NF-L protein, to mediate neuropathic effects have now been determined. In these experiments, expression of the NF-L transgene with only the c-myc mutation was found to have profound disruptive effects on motor neurons of transgenic mice. Moreover, similar neuropathic changes on motor neurons were reproduced in mice bearing a transgene in which the 3'UTR and c-myc mutation of NF-L was appended to a GFP reporter protein. The latter study shows that the neuropathic effects of the mutant NF-L transgene are due to elements in the NF-L transcript, not to the expression of NF-L protein. Further, a less severe form of motor neuron degeneration was seen in mice bearing a chimeric transgene in which the NF-L 3'UTR was appended to the GFP reporter gene. These findings confirm the presence of elements in the NF-L 3'UTR with neuropathic effects on motor neurons of transgenic mice and indicate the neuropathic effects are enhanced by insertion of the c-myc mutation in the transgene. The results indicate that the milder form of motor neuron degeneration in mice bearing a wild-type NF-L transgene (Xu et al., *Cell*, 1993, 73:23–33) can also be attributed to neuropathic effects of an element in the NF-L 3'UTR. Finally, biochemical studies now show that similar stability determinants are present in the 3'UTR of the NF-L and NF-H transcripts, thus indicating that motor neuron degeneration from overexpression of a NF-H transgene (Cote et al., *Cell*, 1993, 35–45) can be attributed to the neuropathic effect of a common element in the NF-H and NF-L 3'UTRs. In summary, it has now been demonstrated that motor neuron degeneration in all three transgenic models arising from expression of different NF transgenes (Xu et al., *Cell*, 1993, 73:23–33; Cote et al., *Cell*, 1993, 35–45; Lee et al., *Neuron*, 1994, 13:975–988) arises from expression of NF transcripts. Further, the neuropathic effects of NF transcripts are due to cis-acting elements that regulate the stabilities of the transcripts and bind common trans-activating factors.

The identification of common cis-acting elements in the 3'UTR of NF mRNAs that lead to motor neuron degeneration in transgenic mice provides important evidence relating to pathways and components thereof which mediate the neuropathic effects. A prime candidate component is the ribonucleoprotein (RNP) complex in brain extracts which binds to the cis-acting element in the 3'UTR of NF-L and NF-H mRNAs that stabilize the transcripts and confer neuropathic effects in transgenic mice. The RNP complexes contain a novel 43 kDa neurofilament mRNA binding protein, referred to as NFRBP-1, that also binds directly to the cis-acting element in the 3'UTR of NF-L and NF-H mRNAs. Insertion of the c-myc mutation into the stability determinant of the NF-L transcript alters the binding of RNP complexes and NFRBP-1 to the stability determinant and disrupts the ability of the stability determinant to regulate the stability of the transcript. Thus, the binding of NFRBP-1 to the NF transcript is closely associated with the stabilization of the transcript and with the enhanced neuropathic effects on motor neurons of transgenic mice that result from presence of the c-myc mutation in the NF-L transgene. The identification of NFRBP-1 and its interactions with other components of neuronal cells and tissue are believed to represent a key link in the pathways leading to motor neuron degeneration in transgenic mice and to motor neuron disease.

SUMMARY OF THE INVENTION

The present invention relates to methods and transgenic animal models for identification, isolation and purification of factors and nucleic acid molecules encoding factors believed to have neuropathic effects on motor neurons. These methods and models can then be used to evaluate the neuropathic effects on motor neurons. For example, using the methods and model of the present invention, cis-acting elements in NF transgenes and trans-acting factors from brain extracts were demonstrated to be causally related to motor neuron degeneration. Identification of factors with neuropathic effect and isolation of the nucleic acid molecules encoding them represents an entirely new approach to the cause and cure of motor neuron degeneration leading to the development of new diagnostics and therapeutics for the treatment of motor neuron diseases.

DETAILED DESCRIPTION OF THE INVENTION

Motor neuron diseases are a group of disorders characterized clinically by weakness and variable wasting of affected muscles without change in sensory function. A number of theses disorders, including Werdnig-Hoffman disease and Kugelberg-Welander syndrome occur in infants or children. The majority of motor neuron diseases, however, occur sporadically in adults between 30 and 60 years of age. There is a degeneration of the anterior horn cell in the spinal cord, the motor nuclei of the lower cranial nerves, and the corticospinal and corticobulbar pathways. These disorders are progressive and usually fatal within 3 to 5 years; death usually results from pulmonary infection. Riluzole, which reduces the presynaptic release of glutamate has been suggested to slow the progression of amyotrophic lateral sclerosis. Otherwise, there is currently no specific treatment for these disorders.

Molecular biology has shown that highly homologous sets of genes regulate the development, differentiation and function of the nervous system in widely divergent species, from fruit flies and round worms to higher vertebrates, including man. Therefore, the identification of genes or gene products causing motor neuron degeneration in mice has immediate diagnostic and therapeutic applications in human disease. It is believed that very similar sets of genes regulate the homeostasis of motor neurons and are causally related to motor neuron degeneration in human disease, such as amyotrophic lateral sclerosis and spinal muscle atrophy. Similar patterns of gene dysfunction may underlie the degeneration of different subsets of neurons in other neurodegenerative diseases.

The direct and indirect effects of altered neurofilament (NF) expression on neuronal degeneration in transgenic mice indicate that pathways in NF expression interact with pathways that maintain the homeostasis of different subsets of neurons. Recently, it has been shown that these pathways are not necessarily related to the expression of NF proteins as previously thought, but rather to the expression of NF mRNAs and to the ribonucleoprotein (RNP) complexes that mediate the processing of neuronal RNA (Cañete-Soler et al., *J. Biol. Chem.* 1998, 273:12650–12654; and Cañete-Soler et al., *J. Biol. Chem.*, 1998, 273:12655–12661).

A cis-acting element at the proximal edge of the 3'UTR of the mouse NF-L mRNA and cognate trans-acting factors from brain extracts have now been identified and implicated in the pathogenesis of motor neuron degeneration in transgenic mice. Based upon experiments described herein, it is now believed that the trans-acting factors not only regulate the expression of NF transcripts but also the expression of gene products maintaining the homeostasis of motor neurons. Expression of cis-acting elements in a NF-L transgene alters the trans-acting factors in motor neurons and disrupt the expression of gene products that maintain motor neuron homeostasis, thereby leading to motor neuron degeneration.

A mouse NF-L transgene was constructed with a 36-bp c-myc tag inserted into the stability determinant of the NF-L mRNA. The transgene was placed behind a strong constitutive promoter and microinjected into the mouse germ line. Nine founder mice (out of 67 pups) were recovered. Two founder mice (pups A and B) were born in an agonal state with markedly distended abdomens. Examination of the intestines revealed extensive dilatation of the midgut in pup A and, to a lesser extent, in pup B. No specific sites of intestinal perforation were identified. Milk products were not present, but fecal content were observed throughout the intestines, indicating that the intestinal dilatation was not due to complete obstruction of the alimentary canal.

Microscopic examination showed that intestinal dilatation was associated with a marked depletion of neurons from the enteric nervous system when the population of enteric neurons was visualized by their immunoreactivity. Multiple sections of midgut revealed either an absence or paucity of neurons in the dilated and thinned intestinal walls of the transgenic pups, compared with non-transgenic littermate controls. The aganglionic and hypoganglionic (loss of >50%) segments of midgut differed only in the extent of neuronal loss. Residual neurons were only observed in the myenteric plexus, although neurons of the myenteric and submucosal plexi were seen in controls. Residual enteric neurons did not display any distinctive pathological features and were difficult to identify with certainty on stained sections.

The effect of this transgene on the development of other neurons, specifically motor neurons, in these animals was also examined. Microscopic examinations at multiple levels of spinal cord revealed a vacuolar degeneration of anterior horn cells in the transgenic pups. The perikarya of altered motor neurons were filled with vacuoles of variable sizes, irregular shapes and sharp borders. Vacuolar degeneration was seen in most anterior horn cells at all levels of spinal cord, more so in pup A than in pup B. Vacuolar changes were not seen in other neurons of the spinal cord, nor in any neurons in spinal cords of non-transgenic littermates. A loosening of neuropil in the vicinity of the vacuolated perikarya may have obscured the presence of vacuolar changes in the neurites of motor neurons. A loosening of neuropil was seen in other regions of spinal cord and in spinal cords of non-transgenic newborn mice. The remarkable preservation of nuclear detail, however, attested to the structural preservation of neuronal cell bodies in immersion-fixed, paraffin-embedded tissues. The large, round nuclei of vacuolated motor neurons had sharply defined nuclear borders, displayed a finely granular chromatin pattern and often contained a very prominent nucleoli. The same nuclear details were observed in vacuolated motor neurons of older transgenic mice without loosening of surrounding neuropil.

Immunoreactivities to mouse NF-L and to the human c-myc tag in vacuolated and control motor neurons of newborn mice were tested with increasing concentrations of primary antibodies to mouse NF-L and the c-myc tag. End products were only observed at titers which produced extensive non-specific staining of the tissues. When the spinal cords of newborn mice were examined with highly sensitive antibodies to phosphorylated epitopes on the NF-H and NF-M subunits, immunoreactivity was detected in white matter tracts along the dorsal and ventral surfaces of spinal cord. Focal NF accumulations in cell bodies or nearby neurites of vacuolated motor neurons were not seen in newborn mice or in the spinal cord of older mice. The limited amounts of motor neuron tissues in newborn mice precluded a biochemical assessment of NF-L protein levels by Western blot.

The extensive vacuolar degeneration of motor neurons in newborn mice was associated with perturbations in target organ development. Differences in skeletal muscle development were readily apparent in comparative examinations of muscles at the level of the distal tibia from transgenic and non-transgenic newborn pups. Whereas the muscle of newborn controls was composed of uniform bundles of muscle fibers with occasional central nuclei, the muscle from the transgenic pups A and B contained numerous small cells without myofibrils interspersed among large fibers with myofibrils. The large fibers had large and hyperchromatic central nuclei that were often associated with perinuclear vacuoles. The features resemble those described during muscle development lacking neurogenic input and have been attributed to a persistence and degeneration of primary myotubes and deficiency of secondary myotube development. Differences between transgenic and non-transgenic muscle were less apparent in musculature from the proximal limbs and along the axial skeleton, suggesting that the changes may reflect a preferential involvement of distal musculature or, possibly, a delay in muscle development.

Further, founder mice and transgenic F1 pups were smaller and less active than their non-transgenic littermates. These traits became apparent during the initial 2–3 week period of postnatal development but did not progress and became less apparent after weaning. An abnormal reflex of flexing the limbs when held by the tail was also observed in these mice. The mice did not develop further weakness or paralysis and were sacrificed along with a non-transgenic littermate at 28 days. Microscopic examination revealed a loss of enteric neurons and vacuolar degeneration of motor neurons in the transgenic pups. Stunted growth was also a useful phenotypic marker of some but not all transgenic pups. When subsequently examined for transgene expression, pups with stunted growth had the highest levels of transgene expression in their respective litters.

Abnormal phenotype in the transgenic animals was found to correlate with expression of the mutant transgene. The highest levels of transgene expression were found in newborn pups with dilated and malformed intestine. RNA protection assays showed the highest level of transgene expression in the brain of pup A, slightly less in the brain of pup B, corresponding with the more severe alterations in pup A. Transgene expression was greater than that of endogenous NF-L expression, although the latter is present at very low levels in neonatal rodent brain. Similar levels of NF-L mRNA were noted in newborn transgenic and non-transgenic littermates, indicating that transgene expression did not appear to alter the expression of endogenous NF-L mRNA. Transgene expression was derived from low transgene copy numbers of 2 and 1 in pups A and B, respectively, as estimated by PCR and Southern blot analyses of genomic DNA.

Expression of the transgene in other founder mice and in transgenic lines was variable. A female founder (mouse C) transmitted the transgene to 4 of 7 F1 pups, but the transgene was not expressed and the abnormal phenotype was not detected in this transgenic line. A male founder (mouse D) was unable to transmit the transgene to three litters of F1 pups. When sacrificed at 3 months, focal vacuolar degeneration was observed in anterior horn cells and a low level of transgene expression was detected in brain. Levels of transgene expression also correlated with the severity of neuropathic changes of enteric and motor neurons in the F1 and F2 progeny.

Neuropathic changes of enteric and motor neurons occurred in three transgenic lines (from founders E, F and G), including eight transgenic pups from the F1 or F2 generations. Two transgenic pups from founder F were less active and without visible milk products in their stomachs, as customarily seen through the thin abdominal wall of newborn suckling mice. When sacrificed on day 2, the absence of milk products was confirmed by direct examination. Instead, the stomachs and small intestines, but not the abdominal cavities, were distended with air, as if the pups had attempted to suckle but had ingested air instead of milk. Microscopically, there was extensive depletion of enteric neurons in the small intestine and vacuolar degeneration of motor neurons, similar to that described in founder mice A and B.

In several instances, either 1 or 2 newborn F1 pups died during the initial 24 hour postnatal period and were probably cannibalized by the mother so that they were not recovered for genomic typing or examination of the tissues. Nonviability of transgenic pups was also suggested in cross-breeding experiments. Initial cross-breeding of founder mice produced F1 litters with only 1 or 2 viable pups and F1 litters with a higher percentage of non-transgenic pups than anticipated. Subsequent cross-breedings of the same founder mice yielded larger F1 litters with close to the anticipated 75% rate of transgene transmission. Transgenic F1 pups, sacrificed at 14 and 28 days, revealed focal losses of enteric neurons and vacuolar changes of motor neurons. The extent of neuropathic changes and corresponding levels of transgene expression were notably less than those observed in founders A and B in the newborn transgenic F1 pups of founder F. Examinations of other tissue, including the kidneys, from the founder mice and transgenic lines were unremarkable.

The effects of a c-myc insert on NF-L mRNA stability in a neuronal cell line were also examined. A full-length NF-L cDNA (NF-L/wt), a cDNA in which 23 bp of distal coding region and 45 bp of proximal 3'UTR were deleted (NF-L/del) and a cDNA containing a 36 bp c-myc insert between the coding region and 3'UTR (NF-L/c-myc) were constructed. The NF-L cDNAs were then placed behind a Tn-10 tetracycline-inducible promoter and stably transfected into a neuronal cell line containing the tTA transactivator cDNA under control of an autoinducible promoter. The system was shown to be highly inducible when tested with a luciferase reporter gene, generating 1,000-fold increases (and decreases) of luciferase activity in the 48 hour interval after withdrawal (and readdition) of tetracycline.

Stability of mRNAs from the NF-L/wt, NF-L/del and NF-L/c-myc cDNAs were compared by inducing transgene expression for 72 hours in the absence of tetracycline, then measuring mRNA levels at varying timepoints after the readdition of the ligand. The NF-L transcript is stabilized by either deleting the entire binding site of the stability determinant (NF-L/del) or by inserting a c-myc tag between the 3'CR and 3'UTR components of the binding site (NF-L/c-myc). The insertion of the c-myc tag is almost as effective as the full deletion in disrupting the function of the determinant.

Experiments were then performed to determine whether the effect of the 36-bp c-myc insert was due to the c-myc sequence per se or to the context of its placement in the stability determinant. The stability of NF-L mRNAs were assessed when the c-myc insert was placed in exon 1 (NF-L/c-myc/BglII) or in the distal 3'UTR (NF-L/c-myc/EcoRI). In both instances, the presence of the c-myc insert did not alter the stability of the transcript. The stability of the NF-L transcript was enhanced, however, when the c-myc tag was inserted into the stability determinant (NF-L/c-myc).

Thus, insertion of the c-myc tag into the stability determinant of the NF-L mRNA appears to alter the stability of the transcript, not due to the presence of the c-myc sequence, but rather due to the placement of a mutation within the stability determinant. Further support of this is derived from the demonstration that the 36 bp c-myc tag in exon 1 does not gel-shift an RNP complex. Instead, placement of the c-myc tag at the end of the coding region alters the RNP complexes that form on the major stability determinant of the transcript.

Gel-shift and cross-linking assays were also undertaken to compare the complexes that form when brain extracts containing RNPs are incubated with probes of wild-type and mutant gene sequences. The RNP complexes that assemble on an RNA probe of NF-L composed of the 23 nt of 3'CR and 45 nt of proximal 3'UTR consist primarily of a set of bands that is competed away by poly(C) homoribopolymers, enhanced in the presence of poly(U) and has been referred to as the C-binding complex (Cañete-Soler et al., *J. Biol. Chem.*, 1998, 273:12655–12661) A similar C-binding complex with a slightly different pattern of electrophoretic migration forms on the probe with a c-myc tag insert between the 3'CR and 3'UTR. While the C-binding complex on the mutant probe is also competed with poly(C) and enhanced in the presence of poly(U), a large percentage of the complex has a slower rate of electrophoretic migration, as if forming a larger aggregate. The formation of an additional slower-migrating component in the C-binding complex on the mutant probe was consistently observed in six gel-shift assays using three different preparations of brain extract that were either freshly prepared or retrieved from storage at −80° C. Formation of slower- and faster-migrating components of the C-binding complex on the mutant probe was observed when gel-shift assays were conducted with 160, 80, 40, 20 or 10 µg of protein. In all instances, at least 35% of radioactivity of the C-binding complex was present in the slower-migrating band.

Insertion of a c-myc tag between the coding region and 3'UTR of the NF-L probe also led to an enrichment of a slow migrating set of bands on the mutant probe that is competed with poly(U) and has been referred to as the U/A-binding complex (Cañete-Soler et al., *J. Biol. Chem.*, 1998, 273:12655–12661). The U/A-binding complex tends to aggregate into a slow-migrating band when assembled in the presence of poly(C). Small amounts of the U/A-binding complex also form on the wild-type probe, but always at lower levels than that formed on the mutant probe.

When the complexes that form on radioactive probes from brain extracts are cross-linked by UV irradiation, digested and examined on denaturing SDS gels, radioactivity from the wild-type and mutant probes are present in a major 43-kDa polypeptide and a minor 80-kDa polypeptide. Since the cross-linking to the 43-kDa polypeptide is competed with poly(C) and the cross-linking to the 80-kDa polypeptide is competed with poly(U), they have been interpreted as core-binding components of the C-binding and U/A-binding complexes, respectively (Cañete-Soler et al., *J. Biol. Chem.*, 1998, 273:12655–12661). Although radioactivities from the wild-type and mutant probes are cross-linked to the same core-binding polypeptides, there are small differences in the amounts of cross-linked radioactivity, especially when formation of the C- or U/A-binding complexes are competed with poly(C) or poly(U). For example, cross-linking to the 80-kDa polypeptide is enhanced in the presence of poly(C) when the wild-type probe is used, but not when the mutant probe is used. Likewise, the addition of poly(U) or poly(A) enhances the cross-linking to the 43-kDa polypeptide from the wild-type probe, but not from the mutant probe. The enhanced cross-linking to core binding polypeptides when formation of C- and U/A-binding complexes are competed, is a characteristic feature of wild-type probes as described by Cañete-Soler et al., *J. Biol. Chem.*, 1998, 273:12655–12661. The lack of a corresponding enhancement in the cross-linking to core binding components from the mutant probe was consistently observed.

Cross-linkage of radioactivity to the 43-kDa polypeptide from the mutant probe was also less than from the wild-type probe. To determine whether the reduction in cross-linkage was due to differences in probe concentration, cross-linkage studies were conducted with increasing amounts of probes that were diluted to the same specific radioactivities. The results indicate that the c-myc mutation leads to a 2-fold reduction in cross-linkage to the 43-kDa polypeptide over a wide range of probe concentrations.

Additional experiments were conducted to confirm the view that neuropathic effects on motor neurons of transgenic mice did not result from expression of protein by the transgene, but rather from expression of mRNA by the transgene, more specifically, from expression of an element in the 3'UTR of the NF-L transgene. Studies were also conducted to show that the presence of the c-myc mutation in the 3'UTR of the NF-L transgene enhanced the neuropathic effects of the transgene on motor neuron degeneration. These results were accomplished by constructing chimeric transgenes in which the 3'UTR of green fluorescent protein (GFP) was replaced with wild-type 3'UTR of mouse NF-L (GFP/NF-L 3'UTR)or with a mutant 3'UTR of mouse NF-L (GFP/c-myc/NF-L 3'UTR) in which a 36-bp c-myc tag was inserted at the proximal edge of the 3'UTR. (Cañete-Soler et al., *J. Neurosci.*, 1999, 19:1273–1283). In both instances, junctional sites were sequenced to confirm the presence and integrity of stop codons at the end of the GFP coding sequences.

The GFP fusion construct with wild-type NF-L 3'UTR (GFP/NF-L 3'UTR), driven by a strong constitutive hCMV promoter, was microinjected into the mouse germ line and 8 founder mice (of 108 pups) were recovered. At 2 weeks, most of the founder mice were smaller and less active than their littermates. Their state of weakness was difficult to assess but their eyes were frequently closed or ptoptic and their fur was rougher than that of non-transgenic littermates. The phenotypes were most prominently displayed between 2 and 3 week. However, the traits were not progressive but tended to recede with further development.

Six transgenic lines were established which reproduced the phenotype. In order to correlate the phenotype with level of transgene expression, F1 and F2 transgenic pups were weighed and assessed for GFP protein expression at 2, 3, 4 and 6 weeks. A semi-quantitative assay for GFP protein expression was conducted by examining immunoreactivity to GFP in white cells of blood smears obtained from tail blood of transgenic pups. The highest levels of transgene expression were associated with more than a 50% reduction in body weight at 2 and 3 weeks. The percentile differences in body weights to non-transgenic controls were progressively less at 4 and 6 weeks. Microscopic examination of founder mice and transgenic lines revealed vacuolar degeneration of anterior horn cells. The findings show that neuropathic effects on motor neurons of transgenic mice result from expression of the NF-L transcript and that the neuropathic cis-acting elements reside in the 3'UTR of the transcript. Furthermore, the similarly of phenotype to that described from overexpression of a mouse NF-L transgene (Xu et al., *Cell*, 1993, 73:23–33) suggests that the neuropathic effects of the full-length NF-L transgene may also reside in the 3'UTR of the transcript.

The GFP fusion construct with the c-myc mutation in the NF-L 3'UTR (GFP/c-myc/NF-L 3'UTR), driven by the hCMV promoter, was also microinjected into the mouse germ line but yielded only 3 founder mice (of 68 pups). The low recovery may have been due in part to smaller litter sizes and deaths of several pups during the early perinatal period. The male founder (C1) mice did not transmit transgene to several litters of progeny and were sacrificed at 9 months. A female founder mice (C2) failed to produce a litter and was also sacrificed at 9 months. The other female founder (C3) was smaller and less active than her littermates. At 2 months, C3 developed progressive weakness and paralysis during the course of her first pregnancy and had to be sacrificed. Microscopically, there was extensive vacuolar degeneration of motor neurons throughout the C3 spinal cord as well as a mild vacuolar degeneration of enteric neurons of the C3 small intestine. Focal vacuolar degeneration was also present in C1 and C2 motor neurons. The vacuolar neuronal degeneration was the same as that produced by a mutant NF-L transgene with a c-myc insert at the proximal edge of the 3'UTR (Cañete-Soler et al., *J. Neurosci.*, 1999, 19:1273–1283). The ability of the same neuropathological changes to be reproduced by a transgene expressing GFP protein indicates that neuropathic effects are not due to expression of NF-L protein. Furthermore, the presence of the c-myc mutation appeared to enhance the neuropathic effects of the NF-L 3'UTR, as evidenced by the severity of vacuolar degeneration in anterior horn cells, by the development of weakness and paralysis in the C3 founder mouse and by a possible lethality of the GFP/c-myc/NF-L 3'UTR transgene.

Data from these experiments provide the first direct causal linkage between an alteration in RNA-processing and a neurodegenerative state in transgenic mice. The findings also identify a cis-acting element in the 3'UTR of mouse NF-L with neuropathic effects and show that the neuropathic element in the NF-L 3'UTR is active when fused to a heterologous reporter gene. A transgenic model is thereby established for probing the aberrant pathways leading to a neurodegenerative phenotype. At the same time, the identification of a neuropathic element in NF-L 3'UTR and the cognate RNA-binding factors provide key biochemical components that can be used to identify other protein or nucleic acid linkages, also referred to herein as factors and/or cofactors, in the pathway leading to motor neuron degeneration.

The present invention relates to the production of a transgenic mouse model for testing nucleic acid sequences for their neuropathic effects on motor neurons, based on the discovery that the neuropathic effects are due to cis-acting elements in the 3'UTR of NF-L mRNA and that the neuropathic elements are active when placed in a heterologous reporter gene. The present invention also relates to methods of identifying additional factors potentially involved in motor neuron degeneration by determining whether the factors interact with the neuropathic elements in the NF-L 3'UTR or the cognate RNA-binding factors and whether the factors alter the binding of RNP complexes from brain extract (e.g., C-binding complex), or components therein (e.g. NFRBP-1) to the neuropathic element in the NF-L 3'UTR. By the term factor it is also meant to include cofactors and nucleic acid sequences encoding factors and/or cofactors. Methods to identify additional factors involved in motor neuron degeneration include, but are not limited to, two- or three-hybrid technologies whereby known proteins (two-hybrid) or RNA binding sites (three-hybrid) are used as "bait" to probe cDNA expression libraries and identify gene products that bind to the proteins or RNA-binding sequences of interest. For the three-hybrid method, the "bait"0 comprises the 68 bp nucleotide sequence of the mRNA stability determinant at the junction of the coding region and 3'UTR of mouse NF-L. The "bait construct" is used to probe cDNA expression libraries prepared from neuronal tissues of human or mouse origin at different stages of maturation. The two-hybrid system utilizes the cDNA sequence of proteins that bind to the 68 nucleotide sequence of the mRNA stability determinant in NF-L as "bait" to identify interactive proteins in the cDNA expression libraries. "Bait" for the two-hybrid method includes, but is not limited to, cDNAs of proteins in brain extracts that bind to the 68 bp sequence in the NF-L stability determinant, namely NFRBP-1, and the 80 kDA protein of the U/A RNP binding complex. By "bait" it is also meant to include cDNAs of proteins that are identified in direct screens of neuronal cDNA expression libraries using the 68 nucleotide sequence of the NF-L mRNA stability determinant as a probe. Factors identified by this method can be isolated and purified and nucleic acid sequences encoding these factors can be cloned, isolated and characterized. By "factors" it is meant proteins and their respective genes that are involved in the posttranscriptional processing of NF or other gene transcripts within the neuron and thereby effecting the expression of the neuronal gene products. The processing of NF or other gene transcripts may involve cleavage, polyadenylation or capping of nascent RNA, splicing or transport of mRNA, localization of mRNA within the cytoplasm, the translation of mRNA or the stability of mRNA in the nucleus or in the cytoplasm. The genes and gene products can then be tested directly for their neuropathic effect in transgenic mice in accordance with the methods described herein or used to identify the critical pathways in motor neurons that maintain neuronal homeostasis, that are susceptible to disruption and that lead to motor neuron degeneration.

The following nonlimiting examples are provided to further illustrate the present invention.

EXAMPLES

Example 1

Construction of Mutant NF-L cDNAs

A full-length mouse NF-L cDNA as described by Cañete-Soler et al., *J. Biol. Chem.*, 1998, 273:1650–12654), in the HindIII/XbaI polylinker sites of pSK+ (Stratagene, La Jolla, Calif.), was used as a PCR template to insert a 36 bp c-myc insert immediately upstream of the stop codon. Overlapping sense and antisense primers to the c-myc insert (upper case), stop codon (underlined) and NF-L sequence (lower case) were synthesized as follows: CTCATTTCT-GAAGAGGACTTGATTtgagcccta ttcccaactattcc (sense; SEQ ID NO:1) and TTCAGAAAT-GAGCTTTTGCTCCCATatctttcttcttagccacc (antisense; SEQ ID NO:2). PCR fragments of upstream (1.7 kb) and downstream (0.5 kb) NF-L sequence were generated using primers to the pSK+ vector sequence flanking the HindIII and XbaI restriction sites. A full-length NF-L cDNA with 36 bp c-myc insert was then generated by PCR using the same flanking primers and the 1.7 kb upstream and the 0.5 kb downstream NF-L PCR fragments as template. The 2.2 kb PCR fragment was gel-excised, cut with HindIII and XbaI and ligated into the HindIII/XbaI sites of a pRC/CMV expression vector (InVitrogen, San Diego, Calif.). The integrity of the NF-L cDNA, c-myc insert and stop codon was confirmed by sequencing both strands of the final construct.

NF-L cDNAs were constructed with the same c-myc insert inserted into BglII site (+828) of exon I (NF-L/c-myc/BglII) or into the EcoRI (+2055) in the distal 3'UTR (NF-L/c-myc/EcoRI). In each instance, sense and antisense oligonucleotides containing the 36 bp c-myc sequence flanked by BglII or EcoRI restriction sites were synthesized, annealed, cut, ligated into the respective restriction sites of the NF-L cDNA and sequenced to determine the orientation of the c-myc insert. Insertion of the c-myc sequence into the BlgII site did not alter the open reading frame of the cDNA. The integrity of all constructs was confirmed by sequencing.

The NF-L/wt and NF-L/c-myc cDNAs were converted into templates for RNA probes by PCR using primers that bracketed the 23 bp of 3'CR and 45 bp of 3'UTR and with the T7 promoter sequence appended to the sense primer. The same strategy was used to construct a control c-myc probe with the 23 bp of upstream and 45 bp of downstream sequence that flanked the c-myc sequence of the BglII site (+828) in exon I, using the NF-L/c-myc/BglII cDNA as template.

Example 2

Determination of mRNA Stability cDNAs with wild-type sequence (NF-L/wt), with the stability determinant deleted (NF-L/del) and with c-myc mutations (NF-L/c-myc, NF-L/c-myc/BlgII, and NF-L/c-myc/EcoRI) were placed into the HindIII/XbaI polylinker sites of a pRC/RSV vector (Invitrogen, San Diego, Calif.) in which the RSV promoter had been replaced with the heptamerized Tn-10 tet operator sequence, as previously described by Cañete-Soler et al., *J. Biol. Chem.,* 1998, 273:12650–12654. The modified vectors (NF-L/wt/tet, NF-L/del/tet and NF-L/c-myc/tet) were transfected into Neuro 2a cells containing a tTA transactivator cDNA with an autoinducible promoter. Cells with transactivator and inducible target transgenes were selected by growth in Zeomycin and Neomycin, respectively, and the presence of the transgenes was monitored by PCR. Multiple clones (>100) with both transgenes were pooled. mRNA was assayed by ribonuclease protection assay and levels of NF-L mRNA were normalized to those of β-actin mRNA in transfected cells. Radioactivity was quantitated by phosphoimager.

Transient transfections were conducted to compare the effects of the c-myc insert when placed in the stability determinant (NF-L/c-myc/tet), in exon 1 (NF-L/c-myc/BglII/tet) or in the 3'UTR (NF-L/c-myc/EcoRI/tet). These vectors were cotransfected with equal amounts of wild-type vector (NF-L/tet) in Neuro 2a cells containing the tTA transactivator expression vector. Expression of the target NF-L cDNAs was activated for 12 hours by growth in the absence of tetracycline and NF-L mRNAs were quantitated at 24 and 48 hours after addition of tetracycline.

NF-L mRNAs in transient transfected cells were quantitated by RT-PCR. RNA was extracted from a Qiagen column and used as template for reverse transcriptase with random hexanucleotides as primers. 20-mer PCR primers were chosen that extended the PCR products across the sites of the c-myc inserts, i.e., from +790 to +925 in exon 1 of NF-L (for NF-L/c-myc/BglII), and from +1701 to +1836 (for NF-L/c-myc) and from +2000 to +2135 (for NF-L/c-myc/EcoR1). Antisense primers were admixed at a 1:50 ratio with $^{32}P$ end-labeled primers. Samples were run for 15, 20 and 25 cycles, separated on 5% acrylamide gels and radioactivity in the PCR products from the mutant and wild-type transcripts quantitated by phosphoimager.

Example 3

Gel-shift and Cross-linking of RNP Components

Full-length RNA probes were uniformly labeled with $^{32}P$-UTP, eluted from acrylamide gels and diluted to $2.5 \times 10^4$ cpm/μl immediately prior to use, as previously described by Cañete-Soler et al., *J. Biol. Chem.,* 1998, 273:12655–12661). Gel-shift and cross-linking assays were conducted with $5 \times 10^4$ cpm of probe and 160 μg protein extracted from rat brain cytosol in 50 mM K acetate, 3 mM Mg acetate, 2 mM dithiothreitol and 20 mM HEPES buffer, pH 7.4, with or without homoribopolymer competitors. RNP complexes on RNA probes were cross-linked by 30 minute exposures on ice at 3 cm under a UV light ($4 \times 10^6 J/cm^2$) and the radioactive polypeptides were denatured by boiling in SDS sample buffer and fractionated by SDS-PAGE. High-speed cytosolic extracts were obtained from rat brain and were used fresh or within a 4-month period of storage at −80° C. Radioactivity in gel-shifted and cross-linked bands were quantitated by phosphoimager.

Example 4

Transgenic Mice

The NF-L cDNA with 36 bp c-myc insert and hCMV promoter was excised with XhoI and XbaI and microinjected into fertilized eggs of B6SJF1/J female mice that had been mated with B6SJF1/J males. Genomic DNA was extracted from tails of 14-day pups and used to detect the transgene by PCR and to estimate transgene copy number by Southern blot. PCR primers spanned the sequence between +1708 and +1815 and generated PCR fragments of 108 and 144 bp from the wild-type and mutant sequence. Genomic DNA was cut with SacI (+1350) and HincII (+1814) to generate fragments of 464 and 500 bp from the endogenous NF-L gene and NF-L transgene, respectively. These fragments were separated on a 2% agarose gel and hybridized with radioactive cDNA probes made by random primed labeling of the SacI/HincII fragment.

Example 5

Tissue Analyses

Transgenic and non-transgenic littermates were euthanized with $CO_2$, their brains excised for RNA protection assay and vertebral columns, abdominal contents and hindlimb musculature were dissected to expose the tissue for optimal fixation. The intestine were fixed in situ by immersion in 10% neutral buffered formalin (NBF) for 24 hours at 4° C., washed and stored in phosphate-buffered saline (PBS) and representative sections were dehydrated and embedded in paraffin. Microscopic sections were stained with hematoxylin and eosin (H&E) or immunostained with PGP9.5 to delineate enteric neurons in accordance with procedures described by Karaosmanoglu et al., *Anat. Rec.,* 1996, 244:470–480). Antibodies to PGP9.5 (Biogenesis Inc., Sundown, N.H.) were applied at a 1:1000 dilution for 1 hour at room temperature and visualized using goat anti-rabbit biotinylated antiserum and the avidin/biotin detection system (Vector Labs, Burlingame, Calif.). The chromaphore was then developed with 3,3'-diaminobenzidine tetrahydrochloride (Sigma Chemical Co., St. Louis, Mo.).

After 4 hours of fixation, the vertebral columns of 14-day, 28-day and adult mice were further dissected to expose the spinal cords directly to NBF prior to washing and storing of tissues in PBS. The spinal cords were separated from the vertebral column, dehydrated, and embedded in paraffin. Paraffin-embedded spinal cords were then cut and positioned in paraffin blocks to obtain serial microscopic cross-sections from the cervical to the lumbar cord. Spinal cords were stained with hematoxylin, hematoxylin and eosin (H&E) or immunostained with primary antibodies to NF-L (N5139, Sigma), to the phosphorylated epitopes on NF-H and NF-M (Ta51 described by Lee et al., *J. Neurosci.,* 1987, 7:3473–3488 and Carden et al., *J. Neurosci.,* 1987, 7:3489–3504) and to the human c-myc tag (AB1, Calbiochem). Secondary antibodies were biotinylated anti-rabbit or anti-mouse IgGs.

Example 6

Expression of Transgenic and Endogenous NF-L mRNA

Brains from transgenic and non-transgenic littermates were homogenized in 4 M guanidinium thiocyanate and total RNA was extracted and stored at −80° C. in formamide as described by Chomczynski, P. and Sacchi, N., *Anal. Biochem.,* 1987, 162:156–159. Levels of mRNA from the endogenous NF-L gene and from the mutant NF-L transgene were quantitated by RNA protection assay using radioactive antisense RNA probes that spanned the 36-bp c-myc insert (+1770). Templates for the RNA probes were generated by PCR and spanned NF-L sequence from +1525 to +1846, including the 36-bp c-myc insert and T7 promoter sequence that was appended to the antisense primer. A full-length RNA probe was uniformly labeled with $^{32}P$-UTP using T7 polymerase as described by Schwartz et al., *J. Biol. Chem.,*

1992, 267:24596–24600 and *J. Biol. Chem.*, 1995, 270:26364–26369. The probe was then separated by electrophoresis, excised from acrylamide gels, eluted overnight into 0.5 M NH$_4$ acetate, 0.1% SDS and 1 mM EDTA and precipitated with et as described by Cañete-Soler et al., *J. Biol. Chem.*, 1998, 273:12655–12661. RNA protection assay was undertaken by hybridizing brain RNA (10–20 μg) with the RNA probe (10$^4$ cpm), as previously described by Schwartz et al., *J. Biol. Chem.*, 1992, 267:24596–24600). Protected fragments of 212 and 322 bp from the wild-type and mutant mRNA were separated by electrophoresis on 7.5% denaturing acrylamide gels and radioactivity of the protected fragments was detected by autoradiogram and quantitated by phosphoimager.

Example 7

Preparation of RNA Probes

Full-length NF cDNAs were used as PCR templates for duplicating sequences in coding region and 3'UTR of each NF subunits and cloning the PCR fragments into pSK+ (Stratagene, La Jolla, Calif.). KpnI and XbaI restriction sites were placed in the flanking sequences of the sense and antisense primers and gel-excised PCR products were cut and cloned into the KpnI/XbaI site of pSK+. Linearized vectors were used as templates for T7 polymerase to generate RNA probes for gel-shift and cross-linking studies. Probes were uniformly labeled with $^{32}$P-UTP, eluted from acrylamide gels and diluted to 2.5×10$^4$ cpm/μl immediately prior to use, as previously described by Cañete-Soler et al., *J. Biol. Chem.*, 1998, 273:12655–12661. Probes for competition studies were generated with a 1:1000 dilution of $^{32}$P-UTP for quantitation, a level of radioactivity that was insufficient to gel-shift a detectable band by autoradiography. Point mutations in the binding site of the C-binding RNP complex were introduced into the template of the H-36 probe by a PCR-based methodology in which the mutations were incorporated into sense and antisense primers as described by Fisher, C. L. and Pei, G. K., *BioTechniques*, 1997, 23:570–574. The integrity of the mutations was confirmed by sequencing the constructs.

Example 8

Construction of Chimeric Transgenes

The effects of the C-binding sites in the NF 3'UTRs on transcript stability were tested using a tetracycline-inducible system as described in Example 2 that was modified so that the changes in transcript stability were reflected by the relative activities of a luciferase reporter gene. Previous studies had shown that the luciferase gene was highly responsive to a tetracycline-inducible promoter. Chimeric transgenes were constructed in a pRC vector (Invitrogen, Carlsbad, Calif.) by placing the luciferase reporter gene behind the tetracycline-inducible promoter and replacing the 3'UTR of the luciferase gene with the 3'UTR from the mouse NF-L or human NF-H gene, with and without deletion of the respective C-binding sites. PCR duplications of wild-type and deleted forms of NF 3'UTRs were generated with flanking SacII and XbaI restriction sites. Deleted forms were created by splicing upstream and downstream PCR fragments that lacked the sequence of the C-binding sites, as described by Cañete-Soler et al., *J. Biol. Chem.*, 1998, 273:12650–12654. Chimeric transgenes with wild-type NF 3'UTRs contained the full-length sequences of probe L680 or H544, while the deleted forms lacked the 68 nt sequence of L68 and the 70 nt sequence of H70. The chimeric constructs with wild-type and deleted forms of the 3'UTR are referred to as Luc/NF-L/wt and Luc/NF-L/del (for the NF-L constructs) and Luc/NF-H/wt and Luc/NF-H/del (for the NF-H constructs). The integrity of the 3'UTR, deletions and junctional sites was confirmed by sequencing the chimeric constructs.

Example 9

Transfections of Neuro 2a Cells with Chimeric Constructs and Assays of Luciferase Activity Studies were conducted on Neuro 2a cells containing a tTA transactivator transgene behind a autoinducible promoter (pUHD15.1M) for activation of tetracycline-responsive promoters. Neuro 2a cells were transfected with the luc/NF-L/wt, luc/NF-L/del, luc/NF-H/wt and luc/NF-H/del constructs, selected with G418 and selected clones (>100) were pooled. The presence of pUHD15.1M and chimeric constructs was monitored by PCR. Neuro 2a cells containing the tTA transactivator transgene and the tetracycline-inducible target vectors were grown for 72 hours in the absence of tetracycline to generate high-levels of luciferase activity. At this timepoint (time 0), tetracycline (0.5 mg/ml) was added to inactivate the chimeric transgenes, and the loss of luciferase activity was assessed at 24, 48 and 72 hours. Cell lysates were harvested in triplicate at each timepoint and levels of luciferase activity were measured using a luciferase assay system (Promega, Madison, Wis.) and Lumat luminometer. Parallel studies were also conducted on Neuro 2a cells containing pUHD15.1M and tetracycline-inducible luciferase transgene with unmodified 3'UTR. Means and standard deviations of 4 experiments were determined.

Example 10

Expression of Untranslated RNA by a Transgene

The mouse NF-L/wt and NF-L/c-myc cDNAs were used as templates for PCR amplification of sequence between +1482 and +2161 of the NF-L/wt cDNA. BglII and XbaI restriction sites were appended to the sense and antisense primers to facilitate insertion of the BglII/XbaI restriction fragments into the BglII/XbaI sites of the multicloning site of the GFP expression vector, pEGFP-C2(Clontech). The sense primer also contained an in-frame TAA stop codon immediately downstream of the BglII site. The integrity of the in-frame stop codon was confirmed by sequencing the junctional sites. The transgenes with strong constitutive hCMV promoter and 3'UTRs were excised with AsnI and MluI and microinjected into fertilized eggs of B6SJF1/J female mice that had been mated with B6SJF1/J males.

Example 11

Assessing Transgene Expression in Transgenic Mice

Genomic DNA was extracted from tail clippings of 14-day pups and used to detect the transgene by PCR and to estimate transgene copy number by Southern blot. At the same time, pups were weighed and a small amount of blood from the clipped tail was admixed with PBS containing 0.5% formalin. Blood samples were pelleted, smeared on glass slides and the white blood cells were monitored for GFP fluorescence and for expression of immunoreactivity to rabbit anti-GFP antibodies (Clontech) at 1:100, 1:400 and 1:1600 dilutions of primary antisera. The presence and abundance of transgene in genomic DNA were correlated with semi-quantitative estimates of transgene expression in white blood cells, with relative body weights and with the appearance of altered movements or behavior. The above parameters, including transgene expression in white blood cells, were assessed at 3, 4 and 6 weeks in transgene pups.

What is claimed is:

1. A transgenic mouse whose genome comprises a nucleic acid sequence encoding a reporter protein and having at the 3' end of the coding region a 36 bp c-myc insert followed by a segment encoding the wild-type neurofilament L (NF-L) 3' UTR, wherein said nucleic acid sequence is operably linked to a promoter and a Tn-10 tet operator sequence and further wherein expression of the nucleic acid sequence results in the mouse exhibiting motor neuron degeneration characterized by the presence or progression of weakness, paralysis or stunting of growth of the transgenic mouse.

2. The mouse of claim 1 wherein the reporter protein is green fluorescent protein.

* * * * *

UNITED STATES PATENT AND TRADEMARK OFFICE
CERTIFICATE OF CORRECTION

PATENT NO.    : 6,323,391 B1
DATED         : November 27, 2001
INVENTOR(S)   : Schlaepfer and Cañete Soler It is certified that error appears in the above-identified patent and that said Letters Patent is hereby corrected as shown below:

Column 11,
Line 52, please delete "bait 0" and insert -- bait --.

Column 15,
Line 5, please delete "with et as" and insert -- with ethanol as --.

Signed and Sealed this

Eleventh Day of March, 2003

JAMES E. ROGAN
*Director of the United States Patent and Trademark Office*